United States Patent
Jayachandra et al.

(10) Patent No.: US 10,344,009 B2
(45) Date of Patent: Jul. 9, 2019

(54) PROCESS FOR THE PREPARATION OF SOFOSBUVIR

(71) Applicant: Mylan Laboratories Limited, Hyderabad (IN)

(72) Inventors: Sureshbabu Jayachandra, Hyderabad (IN); Vipin Kumar Kaushik, Hyderabad (IN); Vijaya Krishna Ravi, Hyderabad (IN); Vikas Chandra Dev, Hyderabad (IN); Saiprasad Kottolla, Hyderabad (IN); Potla Venkata Srinivasa Rao, Hyderabad (IN); Srinivas Vakiti, Hyderabad (IN); Chaitanya Muggu, Hyderabad (IN); Subramanyam Dandala, Hyderabad (IN)

(73) Assignee: Mylan Laboratories Limited, Hyderabad, IN (US)

( * ) Notice: Subject to any disclaimer, the term of this patent is extended or adjusted under 35 U.S.C. 154(b) by 0 days.

(21) Appl. No.: 15/772,833

(22) PCT Filed: Nov. 3, 2016

(86) PCT No.: PCT/IN2016/050380
§ 371 (c)(1),
(2) Date: May 2, 2018

(87) PCT Pub. No.: WO2017/077552
PCT Pub. Date: May 11, 2017

(65) Prior Publication Data
US 2018/0312484 A1    Nov. 1, 2018

(30) Foreign Application Priority Data
Nov. 3, 2015   (IN) .......................... 5940/CHE/2015

(51) Int. Cl.
*C07D 307/33* (2006.01)
*C07D 319/12* (2006.01)
*C07D 307/20* (2006.01)

(52) U.S. Cl.
CPC ......... *C07D 307/33* (2013.01); *C07D 307/20* (2013.01); *C07D 319/12* (2013.01)

(58) Field of Classification Search
CPC ............................ C07D 307/33; C07D 319/12
USPC ........................................................ 549/378
See application file for complete search history.

(56) References Cited

FOREIGN PATENT DOCUMENTS

| CN | 104 610 200 | 5/2015 |
| WO | WO/2006/031725 A2 | 3/2006 |
| WO | 2010049947 | * 5/2010 |

OTHER PUBLICATIONS

Patrick Michel et al: "Butene-2,3-diacetals of glyceraldehyde: a stable alternative to glyceraldehyde acetonide", Arigewaridte Chernie (International ed. in English), Oct. 18, 2002, pp. 3898-3901, Germany.

Emilio Lence et al: "The conformational rigidity of butane-1,2-diacetals as a powerful synthetic tool", Chemical Society Reviews., vol. 37, No. 8, Jan. 1, 2006, p. 1639, Great Britain.

* cited by examiner

*Primary Examiner* — Niloofar Rahmani

(57) ABSTRACT

A process for the preparation of intermediates 9, useful in the synthesis of sofosbuvir, as well as intermediates of formula [12] are disclosed herein.

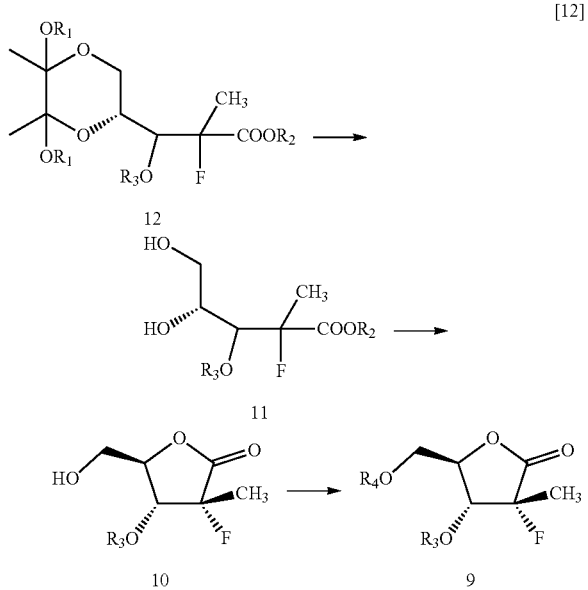

15 Claims, No Drawings

PROCESS FOR THE PREPARATION OF SOFOSBUVIR

CROSS-REFERENCE TO RELATED APPLICATIONS

This application is a national stage entry under 35 U.S.C. § 371 of PCT application no. PCT/IN2016/050380 filed Nov. 3, 2016, which in turn claims the benefit of the earlier filing date of Indian provisional patent application no. 5940/CHE/2015 filed on Nov. 3, 2015.

BACKGROUND OF THE INVENTION

Field of the Disclosure

The present disclosure relates to processes for the preparation of sofosbuvir or its pharmaceutically acceptable salt, which employ novel intermediates. The present invention also provides novel intermediates of sofosbuvir and a process for the preparation thereof.

Description of the Related Art

Nucleoside phosphoramidates are inhibitors of RNA-dependent RNA viral replication and are useful as inhibitors of HCV NS5B polymerase, as inhibitors of HCV replication, and for treatment of hepatitis C infection in mammals. One example of a nucleoside phosphoramidate that inhibits HCV NS5B is sofosbuvir (also called PSI-7977). Sofosbuvir was developed by Pharmasset and is used for the treatment of chronic hepatitis C (CHC) infection, often as a component of a combination antiviral treatment regimen. Sofosbuvir is currently marketed in tablet form as SOVALDI®, in combination with ledipasvir in HARVONI®, and in combination with velpatasvir in EPCLUSA®, all by Gilead Sciences, Inc.

Sofosbuvir is chemically named (S)-isopropyl 2-((S)-(((2R,3R,4R,5R)-5-(2,4-dioxo3,4-dihydropyrimidin-1(2H)-yl)-4-fluoro-3-hydroxy-4-methyltetrahydrofuran-2yl) methoxy)-(phenoxy)phosphorylamino) propanoate and is represented by the following chemical structure (Formula-1):

Formula-1

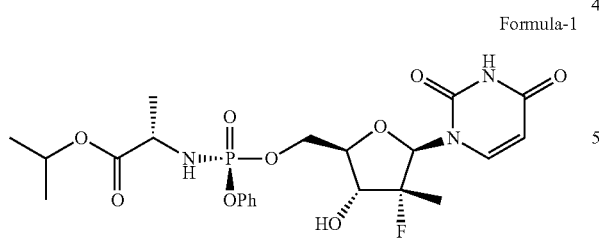

Sofosbuvir and a process for its preparation are disclosed in U.S. Pat. No. 7,964,580 B2 and PCT Publication No. WO 2008/121634 A2, which are hereby incorporated by reference. The present disclosure provides a novel process for the preparation of sofosbuvir or its pharmaceutically acceptable salts that employs novel intermediates.

SUMMARY OF THE DISCLOSURE

In one aspect, the present intention provides a process for the preparation of compound of formula 9:

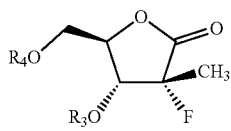

In one embodiment, formula 9 may be prepared by a process that includes the following steps:

a) converting a compound of formula 17 to a compound of formula 16;

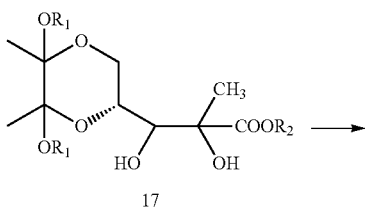

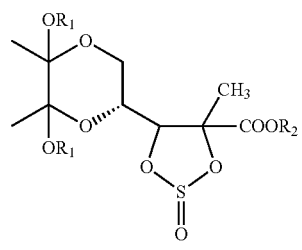

b) oxidizing the compound of formula 16 to get a compound of formula 15;

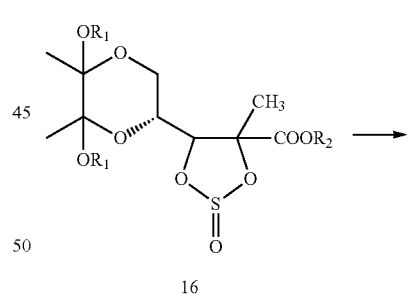

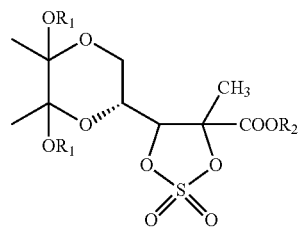

c) fluorinating the compound of formula 15 to obtain fluoro sulfate compound of formula 14;

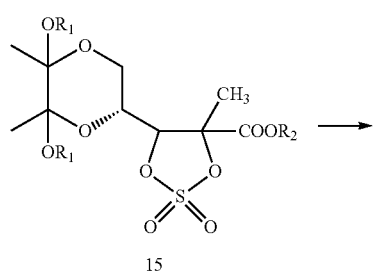

15

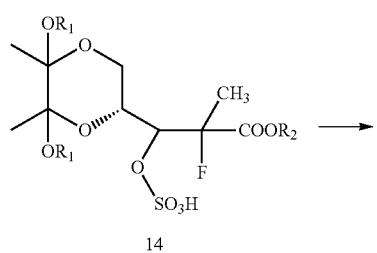

14 d) hydrolyzing the compound of formula 14 to yield a compound of formula 13;

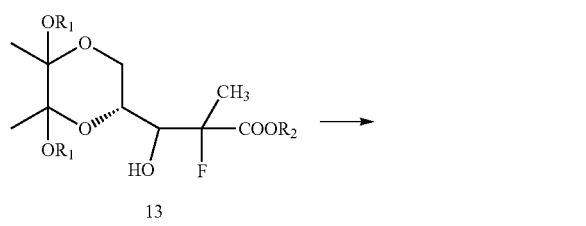

14

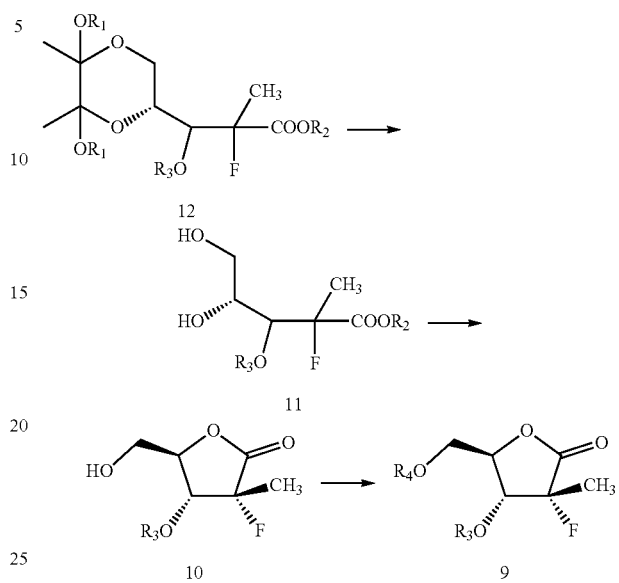

e) protecting the hydroxyl group of the compound of formula 13 to get a compound of formula 12; and

13

12 f) converting the compound of formula 12 to a compound of formula 9

12

11

10    9

Within the context of this embodiment, $R_1$ and $R_2$ are independently selected from hydrogen, $C_1$-$C_{10}$ alkyl, aryl, $C_1$-$C_{10}$ aralkyl; $R_3$ is cinnamoyl or heteroaryl; and $R_4$ is hydrogen, alkyl, aryl, aralkyl, benzoyl, cinnamoyl, or heteroaryl.

Within the context of this embodiment, the compound of formula 17 may be converted to the compound of formula 16 in the presence of a thionyl chloride and a base. The base may be, for example, alkali metal hydroxides, alkali metal carbonates, amine bases, alcoholic amine bases, or mixtures thereof.

Within the context of this embodiment, the oxidizing agent used to convert formula 16 to formula 15 may be sodium hypochlorite, peroxides, or mixtures thereof.

Within the context of this embodiment, the compound of formula 17 may be directly converted to the compound of formula 15 by reacting the compound of formula 17 with a sulfonating agent in the presence of a base. The sulfonating agent may be, for example, sulfuryl chloride, sulfuryl fluoride, or mixtures thereof. Examples of suitable bases include alkali metal hydroxides, alkali metal carbonates, amine bases, alcoholic amine bases, and mixtures thereof.

Within the context of this embodiment, the fluorination of the compound of formula 15 to result in the compound of formula 14 may be performed using a fluorinating agent. Examples of suitable fluorinating agents include hydrogen fluoride, tetraethylammonium fluoride, tetrabutylammonium fluoride, and mixtures thereof.

Within the context of this embodiment, the hydrolyzing of formula 14 may be carried out in the presence of an acid. Examples of suitable acids include hydrochloric acid, hydrobromic acid, sulfuric acid, formic acid, acetic acid, fumaric acid, oxalic acid, and mixtures thereof.

Within the context of this embodiment, the step of converting the compound of formula 12 to the compound of formula 9 may be carried out using an acid. The acid may be, for example, hydrochloric acid, hydrobromic acid, sulfuric acid, formic acid, acetic acid, trifluoro acetic acid, fumaric acid, oxalic acid, or mixtures thereof.

In another aspect, the present invention provides a compound of formula 12a:

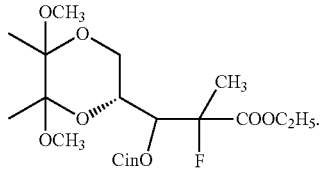

12a

DETAILED DESCRIPTION OF THE DISCLOSURE

It is to be understood that the description of the present invention has been simplified to illustrate elements that are relevant for a clear understanding of the invention, while eliminating, for purposes of clarity, other elements that may be well known.

The present invention encompasses novel synthetic schemes for the synthesis of sofosbuvir. Within the context of the present invention, novel intermediates are generated as part of the novel synthetic schemes. Together, these schemes and intermediates provide an improved, efficient method for the synthesis of sofosbuvir.

In one aspect, the present invention provides a novel process for the preparation of sofosbuvir of formula 1, using novel intermediates, in high yield and with high chemical and enantiomeric purity.

More specifically, the present disclosure provides a process for the preparation of intermediate of formula 9, shown below:

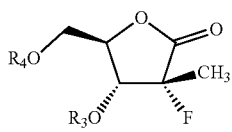

9

In one embodiment, formula 17 may be converted to compound of formula 16, which, upon oxidation, yields a compound of formula 15. In another embodiment, the compound of formula 17 may be directly converted to compound of formula 15.

The compound of formula 15 may then be fluorinated to give a compound of formula 14 which is then converted to compound of formula 13. The compound of formula 13 may be then converted to compound of formula 9 by protecting the hydroxyl group, cleaving the dioxane ring, cyclizing, then protecting the remaining hydroxyl group. The compound of formula 9 may then optionally be converted to sofosbuvir or pharmaceutically acceptable salts thereof by methods known in the art or by the method described herein.

In one embodiment, the present disclosure provides a process for the preparation of compound of formula 9, which may include the following steps:

a) directly or indirectly converting a compound formula 17 to a compound of formula 15;

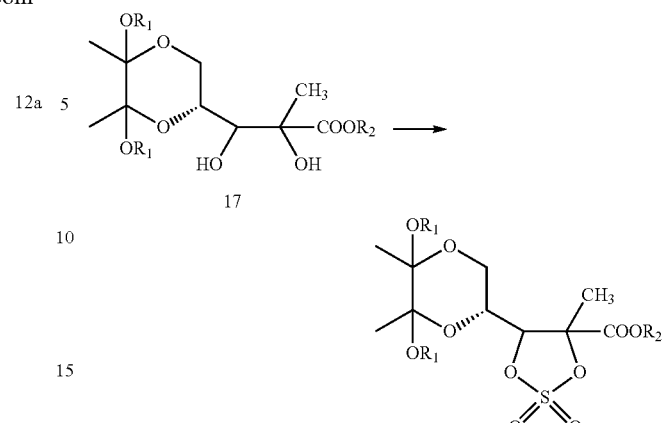

17

15 b) fluorinating formula 15 to obtain formula 14;

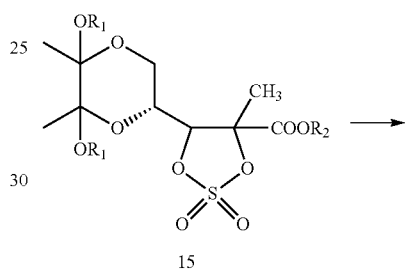

15

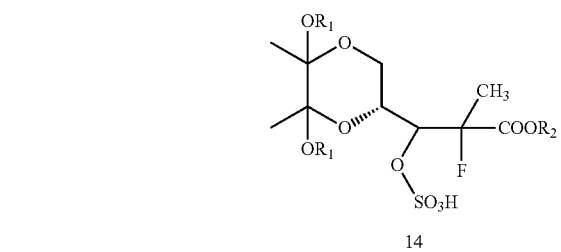

14 c) hydrolyzing formula 14 to yield formula 13;

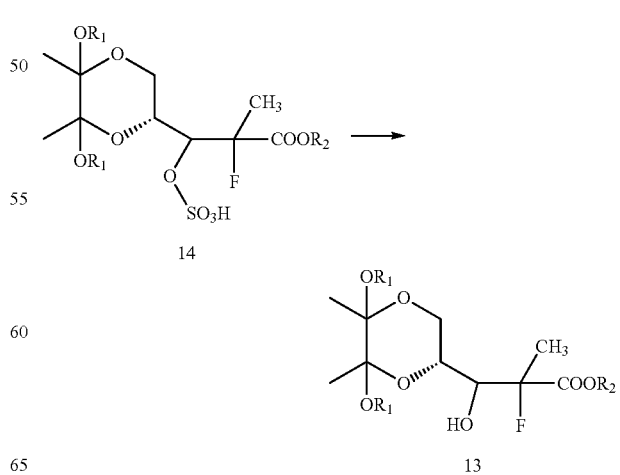

14

13 d) protecting the hydroxyl group of formula 13 to get compound of formula 12; and

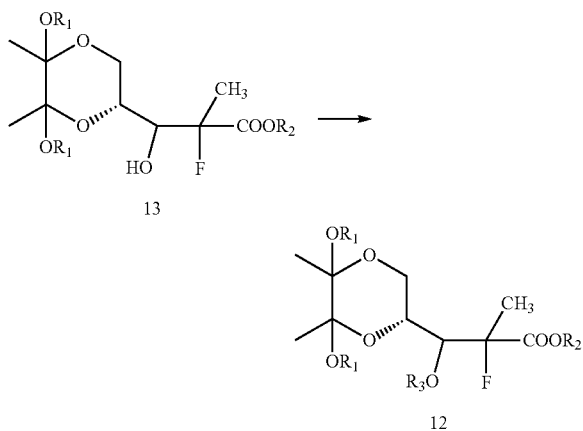

e) converting the compound of formula 12 to a compound of formula 9.

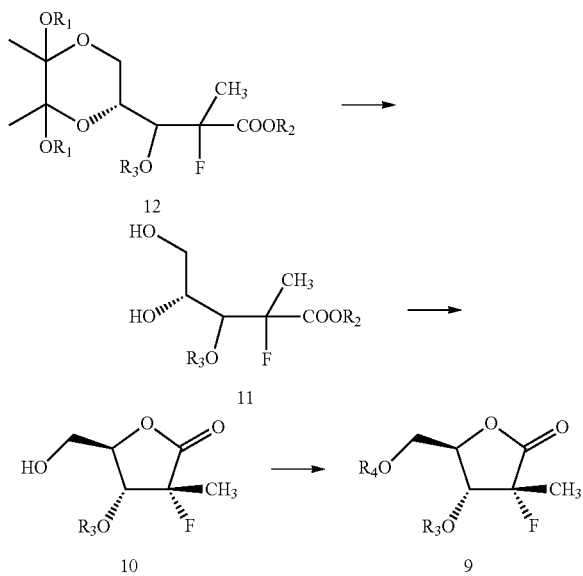

Within the context of this embodiment, $R_1$, $R_2$, $R_3$, and $R_4$ are hydroxy protecting groups and may be the same as or different from one another. Examples of suitable hydroxy protecting groups, as well as suitable conditions for protecting and deprotecting, can be found in prior art, such as J. F. W. McOmie, "Protective Groups in Organic Chemistry", Plenum Press, London and New York 1973; T. W. Greene and P. G. M. Wuts, "Protective Groups in Organic Synthesis", Third edition, Wiley, New York 1999; "The Peptides"; Volume 3 (editors: E. Gross and J. Meienhofer), Academic Press, London and New York 1981; in "Methoden der organischen Chemie", Houben-Weyl, 4th edition, Vol. 15/1, Georg Thieme Verlag, Stuttgart 1974; H.-D. Jakubke and H. Jescheit, "Aminosauren, Peptide, Proteine", Verlag Chemie, Weinheim, Deerfield Beach, and Basel 1982; and Jochen Lehmann, "Chemie der Kohlenhydrate: Monosaccharide and Derivate", Georg Thieme Verlag, Stuttgart 1974.

For example, in some embodiments, $R_1$ and $R_2$ are independently selected from hydrogen, alkyl, aryl, and aralkyl, $R_3$ is a cinnamoyl or a heteroaryl group, and $R_4$ is selected from hydrogen, alkyl, aryl, aralkyl groups, benzoyl, cinnamoyl, and heteroaryl groups.

The term "alkyl" as used herein and throughout the disclosure, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "aryl," as used herein, means a monocyclic (i.e., phenyl), bicyclic, or tricyclic ring fused or bridged system containing at least one phenyl ring. Non-phenyl rings that are part of a bicyclic or tricyclic ring system may be fully or partially saturated, may contain one or more heteroatoms, each selected from N, S, and O, and may be optionally substituted with one or two oxo and/or thia groups. Examples of aryl groups include phenyl, napthyl, anthracenyl, and fluorenyl.

The term "aralkyl" as used herein, means an aryl group, as defined herein, appended to the parent molecular moiety through an alkyl group, as defined herein. Representative examples of aralkyl include, but are not limited to, benzyl, 2-phenylethyl, 3-phenylpropyl, fluorenylmethyl and 2-naphth-2-ylethyl.

The term "heteroaryl," as used herein, means a monocyclic, bicyclic, or tricyclic ring system containing at least one heteroaromatic ring. Any additional rings that are part of a bicyclic or tricyclic ring system may be fully or partially saturated or may be aromatic rings, and each may optionally contain one or more heteroatoms, each selected from N, S, and O. Representative examples of monocyclic and bicyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, triazinyl. benzimidazolyl, benzofuranyl, benzothienyl, benzoxadiazolyl, benzoxathiadiazolyl, benzothiazolyl, cinnolinyl, dihydroquinolinyl, furopyridinyl, indazolyl, indolyl, isoquinolinyl, naphthyridinyl, quinolinyl, purinyl, and tetrahydroquinolin-yl.

Within the context of this embodiment, a compound of formula 17 may be converted to a compound of formula 15. This may be carried out as a two-step process or by direct conversion.

Two-step Process

Within the context of this embodiment, a compound of formula 17 may be converted to a compound of formula 15 by a two-step process. This may be carried out by first converting a compound of formula 17 to a compound of formula 16.

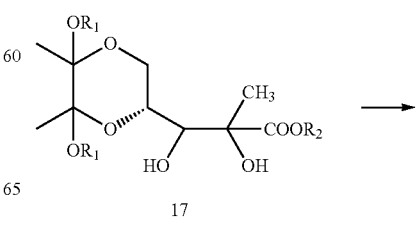

-continued

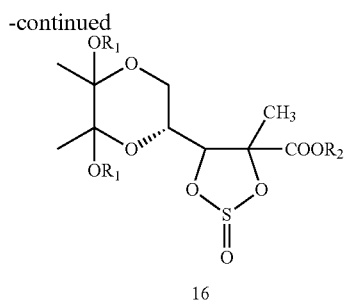

16

The compound of Formula 16 may then be oxidized to yield a compound of formula 15.

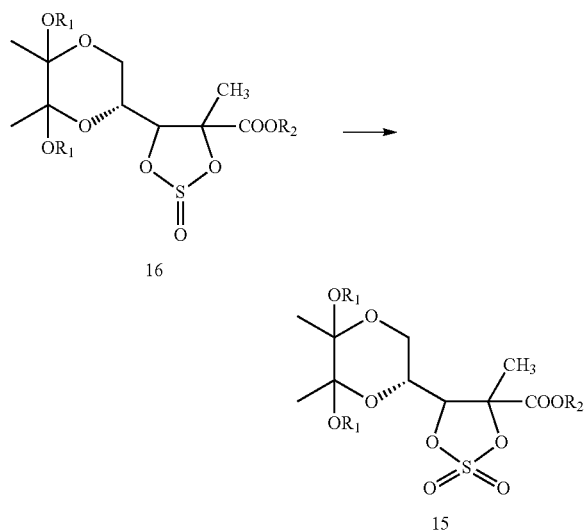

Within the context of the two-step conversion process, compound of formula 17 may be converted to a compound of formula 16. This may be carried out by treating the compound of formula 17 with a thionyl chloride in the presence of a base. Within the context of this embodiment, the base employed may be, for example, alkali metal hydroxides, alkali metal carbonates, amine bases, or mixtures thereof. Examples of suitable alkali metal hydroxides include sodium hydroxide, potassium hydroxide, and mixtures thereof. Examples of suitable alkali metal carbonates include sodium carbonate, potassium carbonate, and mixtures thereof. Examples of suitable amines include triethylamine, pyridine, and mixtures thereof. One of skill in the art will recognize numerous additional bases that may be useful. In certain embodiments, it has been found that triethyl amine is a particularly useful base. In some embodiments this reaction is carried out for about 60 minutes at about 0-5° C.

Next, the compound of formula 16 may be oxidized with an oxidizing agent to obtain formula 15. Within the context of this embodiment, the oxidizing agent employed may be, for example, sodium hypochlorite, peroxides, or mixtures thereof. In certain embodiments, it has been found that sodium hypochlorite is a particularly useful oxidizing agent. One of skill in the art will recognize numerous well-known oxidizing agents that may be useful within the context of the present invention.

Direct Conversion

Within the context of this embodiment, the compound of formula 17 may also be converted to the compound of formula 15 directly.

Within the context of the direct conversion process, the compound of formula 17 may be treated with a sulfonating agent in the presence of a base. Within the context of this embodiment, the sulfonating agent may be, for example, thionyl chloride, sulfuryl chloride, sulfuryl fluoride, or mixtures thereof. One of skill in the art will recognize numerous additional sulfonating agents that may be useful. In certain embodiments, it has been found that sulfuryl chloride is a particularly useful sulfonating agent. Within the context of this embodiment, the base may be, for example, an alkali metal hydroxide, an alkali metal carbonate, an amine, an alkoxide, or mixtures thereof. One of skill in the art will recognize numerous additional bases that may be useful. In certain embodiments, it has been found that triethylamine is a particularly useful base.

This reaction may be carried out in a suitable solvent. One of skill in the art will be familiar with a variety of suitable solvents that would be useful for this reaction. For example, in some embodiments, the solvent is acetonitrile.

Next, the compound of formula 15 may be treated with a fluorinating agent to get a compound of formula 14. Within the context of this embodiment, the fluorinating agent may be, for example, triethylamine trihydrofluoride, hydrogen fluoride, tetraethylammonium fluoride, tetrabutylammonium fluoride, or mixtures thereof. One of skill in the art will recognize numerous well-known fluorinating agents that may be useful within the context of the present invention. In some embodiments, it may be useful to carry out this reaction for about 5-6 hours at about 85-90° C.

Formula 14 may then be hydrolyzed with an acid or a base to obtain formula 13. One of skill in the art will be able to adjust reaction conditions and times to achieve appropriate yields. Within the context of this embodiment, the acid employed may be, for example, a weak inorganic acid, a strong inorganic, or an organic acid. In some embodiments, the acid may be hydrochloric acid, hydrobromic acid, sulfuric acid, formic acid, acetic acid, fumaric acid, oxalic acid, or mixtures thereof. One of skill in the art will recognize numerous well-known acids that may be useful within the context of the present invention.

This reaction may be carried out in a suitable solvent. One of skill in the art would be familiar with a variety of solvents that may be useful for carrying out this reaction. For example, in some embodiments, tetrahydrofuran is used.

Next, the hydroxyl group of the compound of formula 13 may be protected to obtain a compound of formula 12. One of skill in the art will be familiar with suitable protecting groups and be able to adjust reaction conditions and times to achieve appropriate yields based on the nature of the protecting agent. For example, examples of suitable hydroxy protecting groups, as well as suitable conditions for protecting and deprotecting, can be found in prior art, such as J. F. W. McOmie, "Protective Groups in Organic Chemistry", Plenum Press, London and New York 1973; T. W. Greene and P. G. M. Wuts, "Protective Groups in Organic Synthesis", Third edition, Wiley, New York 1999; "The Peptides"; Volume 3 (editors: E. Gross and J. Meienhofer), Academic Press, London and New York 1981; in "Methoden der organischen Chemie", Houben-Weyl, 4th edition, Vol. 15/1, Georg Thieme Verlag, Stuttgart 1974; H.-D. Jakubke and H. Jescheit, "Aminosauren, Peptide, Proteine", Verlag Chemie, Weinheim, Deerfield Beach, and Basel 1982; and Jochen Lehmann, "Chemie der Kohlenhydrate: Monosaccharide and Derivate", Georg Thieme Verlag, Stuttgart 1974.

In some embodiments, alkyl, aryl, aralkyl, heteroaryl, cinnamoyl, or benzoyl groups are used as hydroxyl protecting groups.

In particularly useful embodiments, the compound of formula 13 is treated with cinnamoyl chloride, 4-dimethylaminopyridine, and triethylamine in acetonitrile to result in the compound of formula 12 protected by a cinnamoyl group as $R_3$.

Next, according to this embodiment, the compound of formula 12 may then be converted to compound of formula 9. This may be carried out by cleavage of dioxane ring, followed by cyclization, then protecting the remaining hydroxyl group with suitable hydroxyl protecting group.

Within the context of this embodiment, the conversion of formula 12 to formula 9 may be carried out by first treating the compound of formula 12 with an acid to get a compound of formula 10. Within the context of this embodiment, and as pictured above, formula 11 may be formed in situ as an intermediate in this reaction. However, treatment of formula 12 with an acid will cause the reaction to proceed to the formation of formula 10.

Within the context of this embodiment, the acid may be, for example, a weak inorganic acid, a strong inorganic acid, an organic acids, or mixtures thereof. For example, hydrochloric acid, hydrobromic acid, sulfuric acid, formic acid, acetic acid, trifluoroacetic acid, fumaric acid, oxalic acid, or mixtures thereof may be used as an acid. One of skill in the art will recognize numerous acids that may be useful within the context of the present invention.

This reaction may be carried out in the presence of a suitable solvent. For example, water may be used. One of skill in the art would be familiar with a variety of solvents that may be useful for carrying out this reaction.

Next, the hydroxyl group on formula 10 may be protected to get formula 9. One of skill in the art will be able to adjust reaction conditions and times to achieve appropriate yields based on the nature of the protecting agent.

For example, in some particularly useful embodiments, formula 10 is treated with 4-dimethylaminopyridine, cinnamoyl chloride, and triethylamine in acetonitrile to result in formula 9, protected with a cinnamoyl group as $R_4$. In other particularly useful embodiments, formula 10 is treated with 4-dimethylaminopyridine, benzoyl chloride, and triethylamine in acetonitrile to result in formula 9, protected at the $R_4$ position with a benzoyl group.

In another aspect, the present invention provides a process for the preparation of sofosbuvir, which may be carried out by a process that includes the following steps:

a) transforming a compound of formula 9 into a compound of formula 7 through reduction and chlorination;

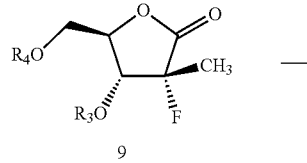

9

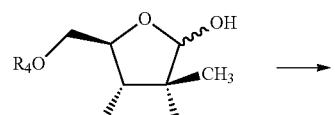

8

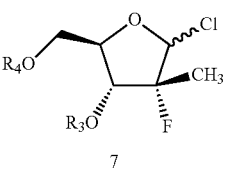

7 b) reacting the compound of formula 7 with O-trimethyl silyl-$N^4$-benzoylcytosine in the presence of a Lewis acid to get a compound of formula 5;

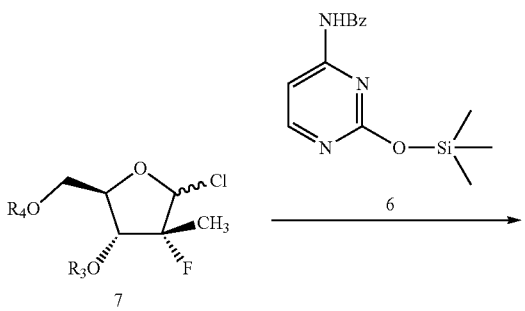

c) hydrolyzing the compound of formula 5 to get a compound of formula 4;

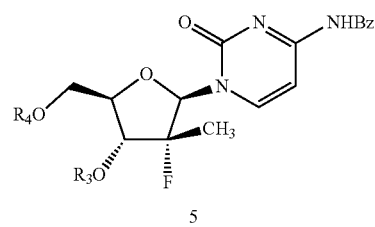

5

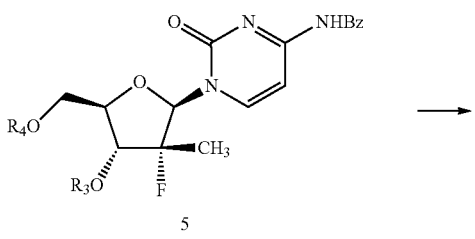

4 d) reacting the compound of formula 4 with a compound of formula 3 to get a compound of formula 2; and

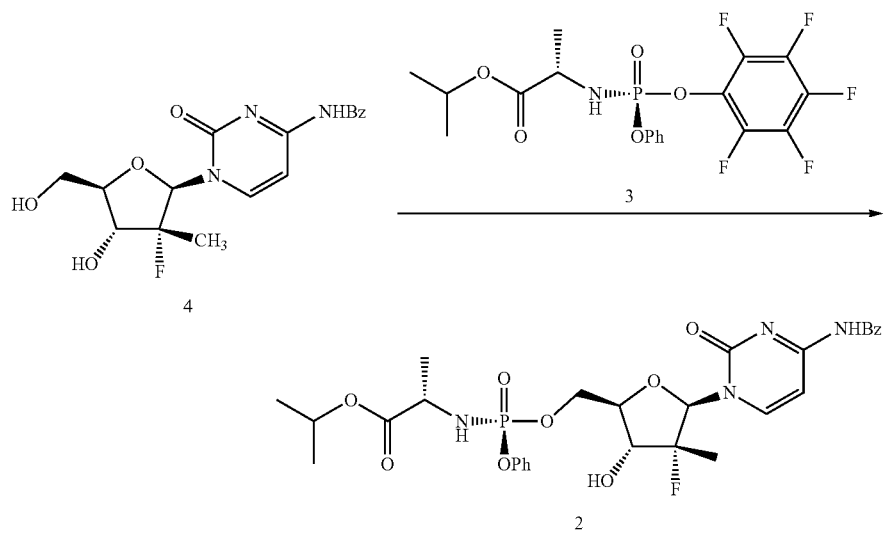

e) hydrolyzing the compound of formula 2 to get sofosbuvir (formula 1).

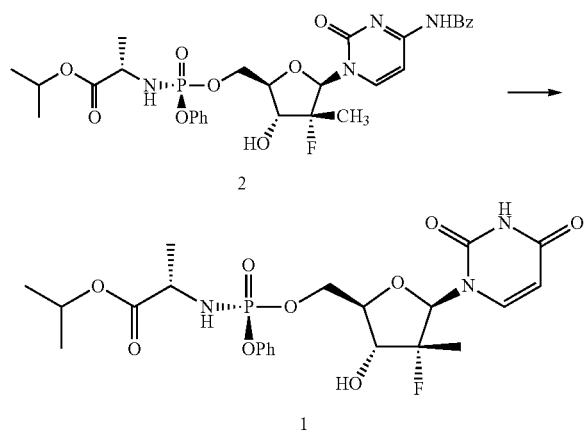

Within the context of this embodiment, $R_3$ is a cinnamoyl or heteroaryl group and $R_4$ is hydrogen, alkyl, aryl, aralkyl groups, benzoyl, cinnamoyl, or a heteroaryl group.

According to the this embodiment, formula 9 may be converted to formula 7 by first treating formula 9 with a reducing agent to get formula 8. This reaction may be carried out in the presence of a suitable solvent. Examples of suitable solvents include 2,2,2-trifluoroethanol. Examples of suitable reducing agents include organoaluminum compounds, for example, sodium bis(2-methoxyethoxy)aluminum hydride (e.g., RED-Al®, Synhydrid, Vitride). One of skill in the art will recognize numerous additional reducing agents and solvents that may be useful. In some embodiments, this reaction is carried out for about 2 hours at about −20 to −5° C.

This reaction may be carried out in the presence of a suitable solvent, for example, toluene, xylene, benzene, and mixtures thereof.

The compound of formula 8 may then be chlorinated with a chlorinating agent to obtain a compound of formula 7. Within the context of this embodiment, the chlorinating agent may be, for example, oxalyl chloride, thionyl chloride, sulfuryl chloride, or mixtures thereof. In certain particularly useful embodiments, oxalyl chloride is used as a chlorinating agent to obtain the compound of formula 7. One of skill in the art will recognize numerous well-known chlorinating agents that may be useful within the context of the present embodiment.

This reaction may be carried out in the presence of a suitable reagent and a suitable solvent. One of skill in the art will be familiar with suitable reagents and solvents for this reaction. For example, suitable solvents include, but are not limited to, methylene dichloride, dichloroethane, chloroform, and mixtures thereof. In some embodiments, this reaction is carried out in the presence of N,N-dimethylformamide.

Next, compound of formula 7 may be treated with O-trimethyl silyl-$N^4$-benzoyl cytosine in the presence of a Lewis acid to obtain a compound of formula 5. Within the context of the present invention, the O-trialkyl silyl-$N^4$-benzoyl cytosine may be added as a single reagent or created in situ by adding $N^4$-benzocytosine and a hexaalkyldisilazane. In certain embodiments, in situ preparation of O-trimethyl silyl-$N^4$-benzoyl cytosine is carried out by combining $N^4$-benzocytozine and hexamethyldisilazane. Within the context of this embodiment, examples of suitable Lewis acids include tin(IV) chloride, aluminum chloride, titanium (IV) chloride, iron(III) chloride, zinc chloride, and mixtures thereof. Again, one of skill in the art will recognize numerous additional Lewis acids that may be useful. In certain embodiments, it has been found that tin (IV) chloride is a particularly useful Lewis acid.

This reaction may be carried out in the presence of a suitable solvent, for example, chlorobenzene.

Next, compound of formula 5 may be hydrolyzed in the presence of a base to get a compound of formula 4. Within the context of this embodiment, the base may be, for example, an alkali metal hydroxides. Examples of suitable alkali metal hydroxides include sodium hydroxide, potassium hydroxide, lithium hydroxide, and mixtures thereof. One of skill in the art will recognize numerous well-known bases that may be useful within the context of the present invention. In certain embodiments, sodium hydroxide is used as the base.

This reaction may be carried out in the presence of a suitable solvent, for example, an alcohol, water, or mixtures thereof. In some embodiments, methanol is used.

According to the present embodiment, compound of formula 4 may then be condensed with a compound of formula 3 to yield formula 2 (N-benzoyl sofosbuvir). This may be carried out in the presence of magnesium chloride or tert-butyl magnesium chloride and a solvent.

Within the context of the present embodiment, the solvent may be a polar aprotic solvent, for example, tetrahydrofuran, acetonitrile, dimethyl formamide, or mixtures thereof. One of skill in the art will recognize numerous additional polar aprotic organic solvents that may be useful. In certain embodiments, it has been found that tetrahydrofuran is a particularly useful solvent. In some embodiments, this reaction is carried out for about 30 minutes to 60 minutes at about 20-25° C.

Next, the compound of formula 2 may be hydrolyzed to yield sofosbuvir. Within the context of this embodiment, this reaction may be carried out with an aqueous acid, by heating in the presence of water and a neutral organic co-solvent, or a combination of the two processes (i.e., using a neutral co-solvent and an acid in the presence of heat).

Within the context of this embodiment, the aqueous acid may be, for example, hydrochloric acid, hydrobromic acid, sulfuric acid, formic acid, citric acid, acetic acid, fumaric acid, oxalic acid, or mixtures thereof. The neutral organic co-solvent, may be, for example, 1,4-dioxane, 1,2-dimethoxyethane, or mixtures thereof. One of skill in the art will recognize numerous neutral organic co-solvents that may be useful within the context of the present invention. In certain particularly useful embodiments, formula 2 is hydrolyzed by heating in presence of water and 1,2-dimethoxyethane.

Within the context of the present invention, sofosbuvir may be optionally converted to a pharmaceutically acceptable salt of sofosbuvir.

Methods for converting compounds into their salt forms are also well known in the art, and may be carried out, for example, by reacting a free base or free acid moiety on sofosbuvir with a suitable reagent.

For example, in some embodiments, a free base moiety on sofosbuvir can be reacted with a suitable acid to obtain a pharmaceutically acceptable salt of sofosbuvir.

Pharmaceutically acceptable salts of sofosbuvir include as acid addition salts, formed with inorganic acids or organic acids. Examples of suitable inorganic acids include hydrochloric acid, hydrobromic acid, sulfuric acid, nitric acid, phosphoric acid, and the like. Examples of suitable organic acids include glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like. Other examples of pharmaceutically acceptable salts include basic addition salts formed with the conjugate bases of any of the inorganic acids listed above, wherein the conjugate bases comprise a cationic component selected from among $Na^+$, $K^+$, $Mg^{2+}$, $Ca^{2+}$, and $NHgR^-_{4-g}{}^+$; in which $R^-$ is a $C_{1-3}$ alkyl and g is a number selected from among 0, 1, 2, 3, or 4. It should be understood that all references to pharmaceutically acceptable salts include solvent addition forms (solvates), crystal forms (polymorphs), or amorphous forms as defined herein, of the same acid addition salt.

In another embodiment, the present invention provides a process for the preparation of formula sofosbuvir which is shown below in scheme-1:

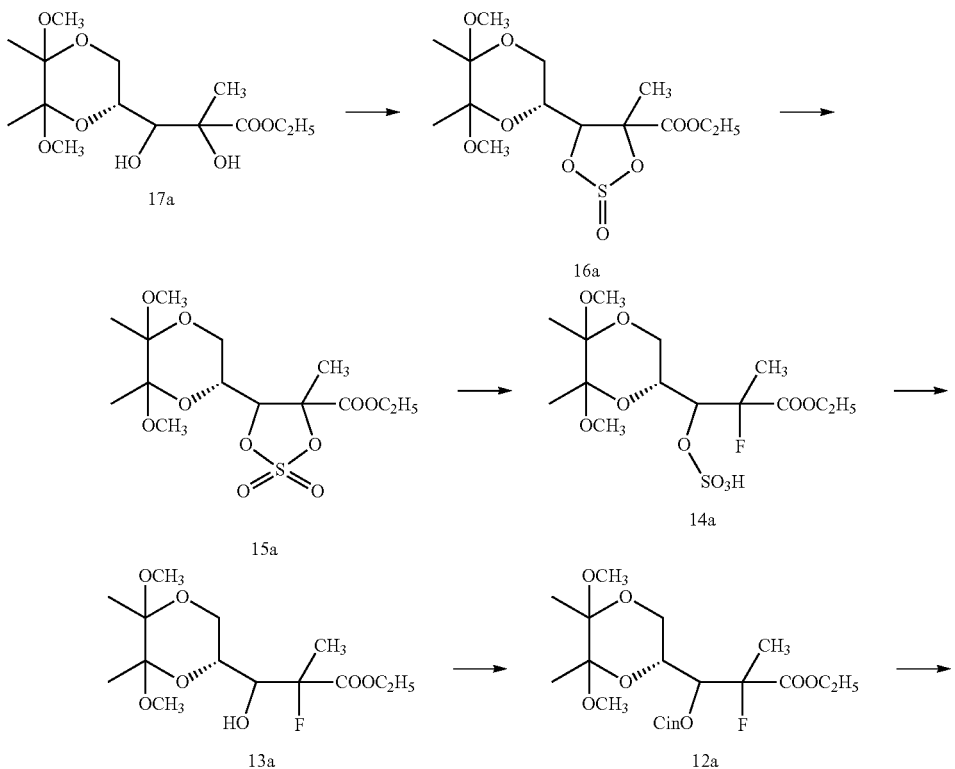

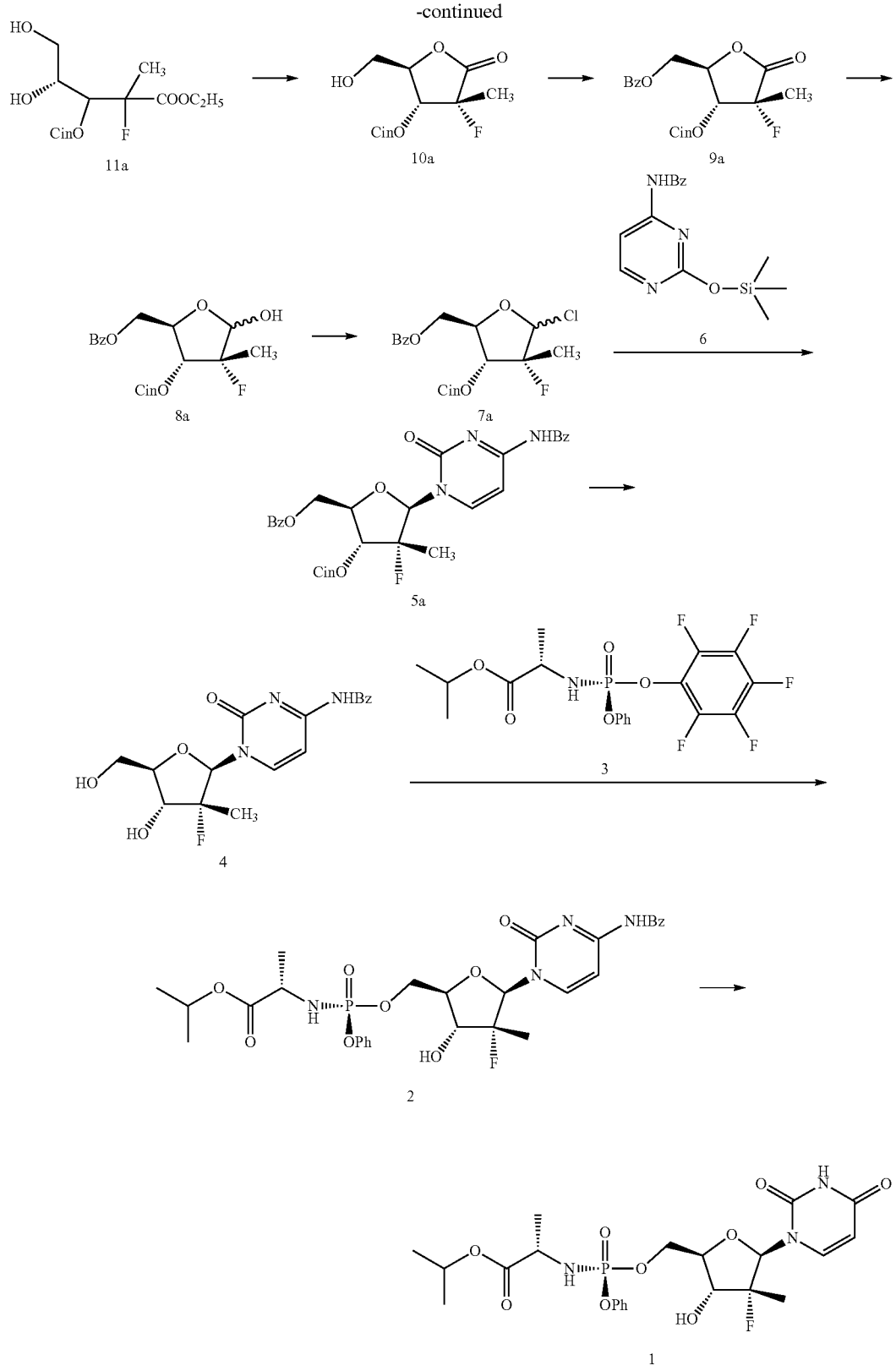
Within the context of this embodiment, "Cin" refers to cinnamoyl protecting groups and "Bz" refers to benzoyl groups.
In another embodiment, the present invention provides a process for the preparation of compound of formula 17, which is shown below in scheme-II:

Scheme-II
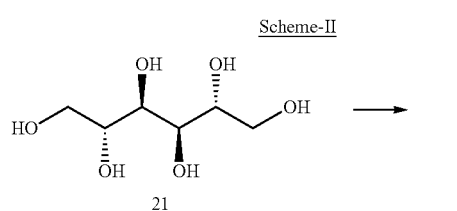
21
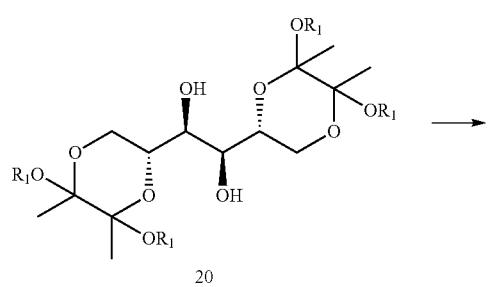
20
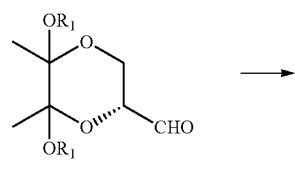
19
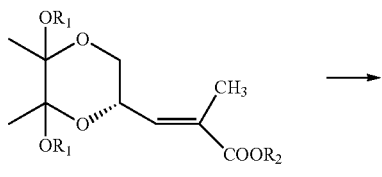
18
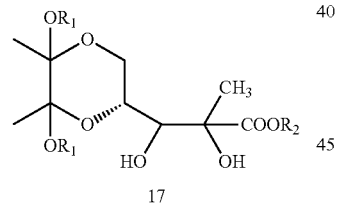
17
Within the context of Scheme-II, $R_1$ and $R_2$ are hydroxyl protecting groups, as defined previously.
In yet another embodiment, the present invention provides a process for the preparation of compound of formula 4, which is shown below in scheme-III:
Scheme-III
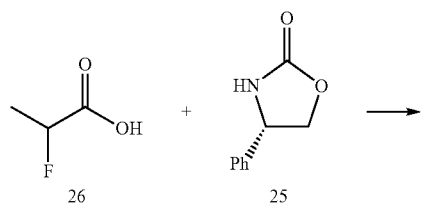
26   25
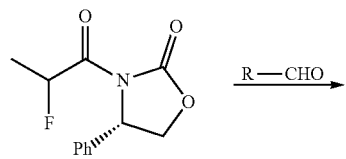
24
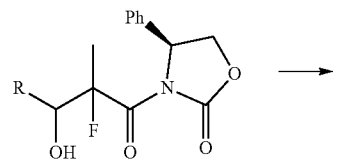
23
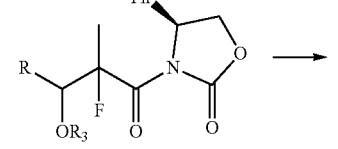
22
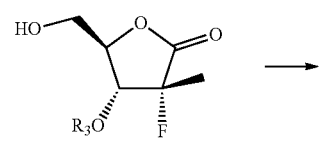
10
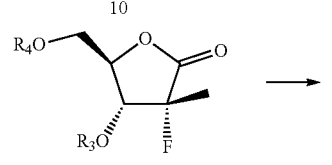
9
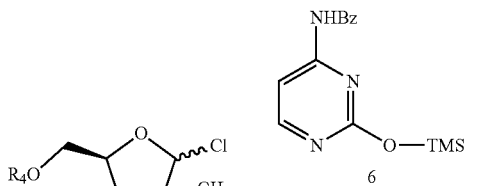
7
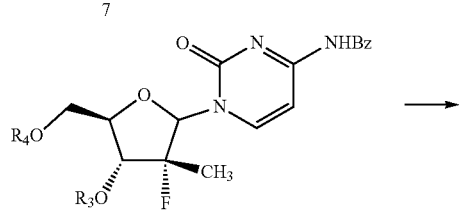
5
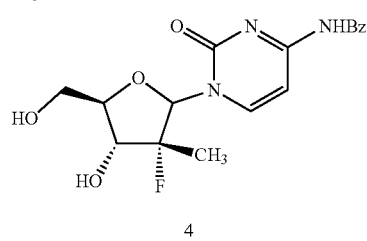
4

Within the context of this embodiment, R₃ is a cinnamoyl or heteroaryl group, R₄ is hydrogen, alkyl, aryl, aralkyl, benzoyl, cinnamoyl, or a heteroaryl group, and R is selected from

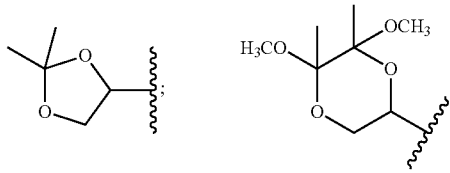

Yet another embodiment of the present invention provides a process for the preparation of compound of formula 4, which is shown below in scheme-IV:

Scheme-IV

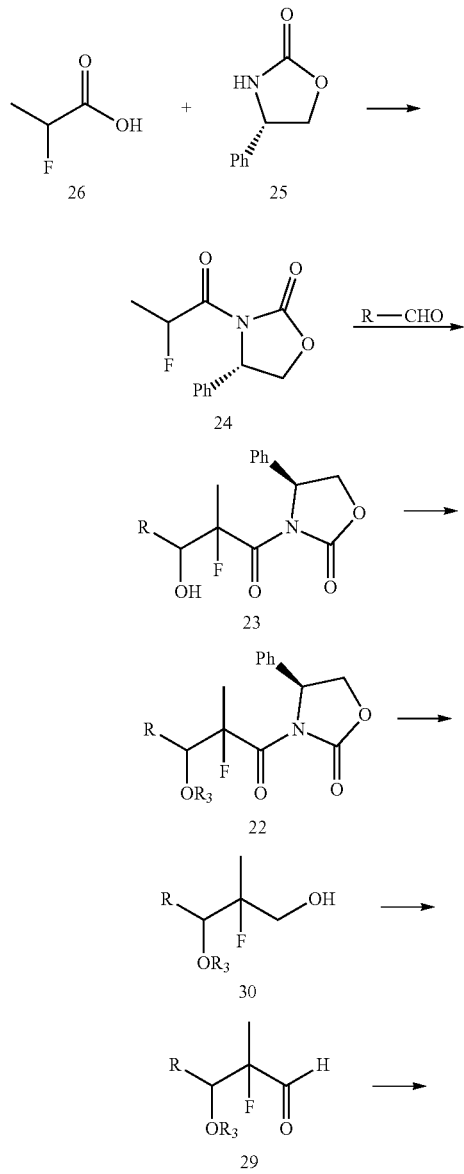

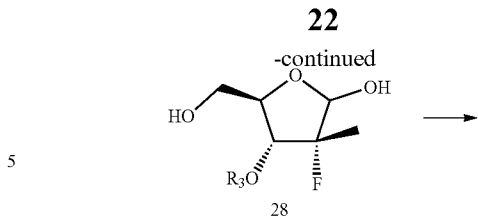

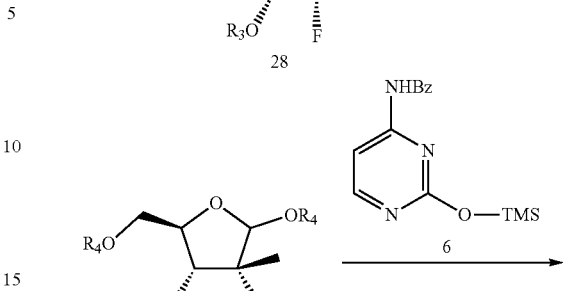

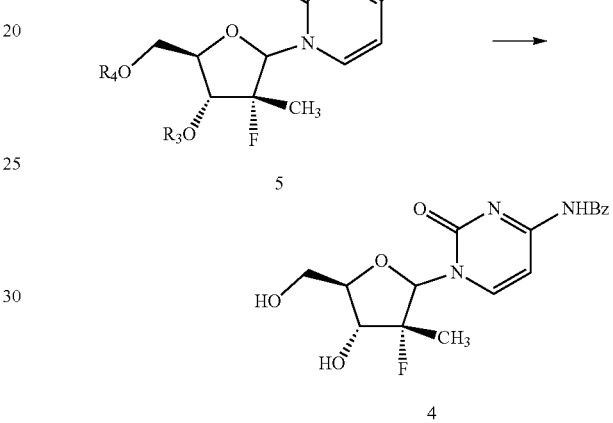

Within the context of Scheme-IV, R₃ is a cinnamoyl or heteroaryl group and R₄ is hydrogen, alkyl, aryl, aralkyl, benzoyl, cinnamoyl, or a heteroaryl group.

Another aspect of the present invention provides amorphous sofosbuvir. Within the context of this embodiment, amorphous sofosbuvir may be prepared by a variety of methods, including, for example, precipitation from a suitable solvent, sublimation, growth from a melt, solid state transformation from another phase, precipitation from a supercritical fluid, and jet spraying. Techniques for crystallization or recrystallization include, for example, evaporation of the solvent, decreasing the temperature of the solvent mixture, rapid drying of the solvent mixture, agitated thin film drying the solvent mixture, freeze drying the solvent mixture, and addition of anti-solvents to the solvent mixture.

The present disclosure further provides a pharmaceutically acceptable salt of sofosbuvir. All theoretically possible tautomer, geometrical isomer, optically active compound, and racemates thereof are also within the scope of the present invention.

With all of the reactions disclosed above, one of skill in the art will recognize that the reaction conditions (e.g., reaction time or temperature) may be adjusted to achieve appropriate yield without undertaking undue experimentation and without departing from the scope of the present disclosure.

The sofosbuvir and pharmaceutically acceptable salts as synthesized by the methods disclosed herein may be useful in the treatment of individuals infected with hepatitis C, as sofosbuvir has been demonstrated to be an effective HCV NS5B polymerase inhibitor. Sofosbuvir may be used single or in combination with other drugs, such as ledipasvir, daclatasvir, ribavirin, pegylated interferon, and velpatasvir.

The sofosbuvir and pharmaceutically acceptable salts thereof may be formulated as a tablet for consumption by patients, where the tablet is formulated having the inactive ingredients of colloidal silicon dioxide, copovidone, croscarmellose sodium, lactose monohydrate, magnesium stearate, mannitol, microcrystalline cellulose, and mixtures thereof. That tablet core may, in some embodiments, be coated with a film that includes polyethylene glycol, polyvinyl alcohol, talc, titanium dioxide, and artificial colorings, such as yellow iron oxide, iron oxide red, FD&C yellow #6 Aluminum Lake, and sunset yellow FCF, and mixtures thereof.

In view of the above description and the examples below, one of ordinary skill in the art will be able to practice the invention as claimed without undue experimentation. The foregoing will be better understood with reference to the following examples that detail certain procedures for the preparation of molecules, compositions, and formulations according to the present invention. All references made to these examples are for the purposes of illustration. The following examples should not be considered exhaustive, but merely illustrative of only a few of the many aspects and embodiments contemplated by the present disclosure.

The intermediates formed during the processes disclosed herein can be characterized by $^1$H NMR analysis. Therefore, samples were analyzed by $^1$H NMR and data were collected on a Bruker 300 MHz Avance NMR spectrometer equipped with 5 mm BBI probe in DMSO or in CDCl$_3$. Data were collected and processed by Topsin-NMR software.

EXAMPLES

Example 1

Preparation of the Compound of Formula 19
($R_1$=$CH_3$)

Under nitrogen atmosphere and stirring, boron trifluoride diethyl etherate (16.2 mL) was added to a mixture of D-mannitol (100 g), anhydrous trimethylorthoformate (243 mL), and 2,3-butanedione (101 mL) in methanol (500 mL) at 25-30° C. After 5 hours of stirring, the reaction mixture was neutralized by triethylamine (16.2 mL) and concentrated under reduced pressure. The obtained residue was dissolved in dichloromethane (2 L) and washed with water (1 L) and aqueous sodium chloride solution. The organic layer was dried over sodium sulfate and concentrated under reduced pressure. The obtained residue (comprising protected mannitol (i.e., diacetonide)) was diluted with dichloromethane (2 L) and saturated aqueous sodium bicarbonate (to produce a 0.5 mL/g solution of diacetonide). Sodium metaperiodate (246 g) was added in lots over a period of 20-30 minutes at 25-35° C. and the resulting mixture was stirred maintaining the temperature below 35° C. After completion of the reaction, 118 g of sodium sulfate was added, the mixture was stirred for 20 minutes, filtered, and the filtrate was washed with 200 mL of dichloromethane. The filtrate was then concentrated under reduced pressure at 40-45° C. to yield ~200 g of an oily residue, which was purified by fractional distillation under reduced pressure (<10 mm Hg).

$^1$H NMR (300 MHz, CDCl3, δ ppm): 1.27 (3H, s), 1.39 (3H, s), 3.27 (3H, s), 3.33 (3H, s), 3.68-3.73 (2H, m), 4.33-4.38 (1H, dd), 9.73 (1H, s).

Example 2

Preparation of
(carbethoxyethylidene)triphenylphosphorane

A mixture of triphenylphosphine (13.1 g), ethyl-2-bromopropionate (10.0 g), toluene (20 mL), and water (50 mL) were heated to 80° C. and stirred for 12 hours maintaining this temperature. After cooling to 50° C., the aqueous layer was separated and washed with toluene (10 mL). The aqueous layer was then cooled to 25-35° C. and the pH was adjusted to 8.0-9.0 with ~10% w/w aqueous sodium hydroxide solution and stirred for 1 hour to precipitate the product. The product was filtered, washed with water (30 mL), and dried at 50° C. under reduced pressure to yield (carbethoxyethylidene)triphenylphosphorane (15 g).

Example 3

Preparation of the Compound of Formula 18
($R_1$=$CH_3$; $R_2$=$CH_2CH_3$)

A solution of the compound of formula 19 ($R_1$=$CH_3$, 10.0 g) in methylene dichloride (20 mL) was added to a solution of (carbethoxyethylidene)triphenylphosphorane (17.7 g) in methylene dichloride (50 mL) at 0-5° C. over a period of 1.5 hours. Thereafter, temperature was raised to 25-35° C. and the reaction mass stirred for 12 hours at this temperature. The resulting reaction mass was concentrated under reduced pressure and the obtained residue was treated with n-heptane (50 mL). The solution was filtered and the obtained filtrate was concentrated at 40-45° C. under reduced pressure to yield the titled product as a light yellow liquid (12.0 g).

$^1$H NMR (300 MHz, CDCl3, δ ppm): 1.26-1.32 (9H, m), 1.90 (3H, s), 3.29 (3H, s), 3.32 (3H, s), 3.37-3.42 (1H, m), 3.63-3.70 (1H, m), 4.14-4.21 (2H, q), 4.75-4.82 (1H, m), 6.61-6.65 (1H, m).

Example 4

Preparation the Compound of Formula 17
($R_1$=$CH_3$; $R_2$=$CH_2CH_3$)

Ethylene glycol (8.6 g), sodium bicarbonate (8.7 g), water (20 mL), and potassium permanganate (5.7 g) were added in portions to a mixture of the compound of formula 18 ($R_1$=$R_2$=$CH_3$, 10 g) in acetone (100 mL) at −10° C. over 2 hours. The resulting solution was stirred for 1 hour at −10° C. and quenched by the addition of 25% w/w aqueous sodium bisulfite solution (20 mL). The resulting solids were removed by filtration and obtained filtrate was concentrated 40-45° C. under reduced pressure. The resultant mass was extracted with ethyl acetate (2×50 mL), dried over anhydrous sodium sulfate, and concentrated under reduced pressure to 40-45° C. to provide the titled compound (10 g).

$^1$H NMR (300 MHz, DMSO-d6, δ ppm): 1.12-1.29 (12H, m), 3.12 (3H, s), 3.17 (3H, s), 3.48-3.56 (2H, m), 3.82-3.95 (1H, m), 4.04-4.07 (2H, q), 4.97-5.04 (3H, m).

Example 5

Preparation of the Compound of Formula 15
(Two-Step Process from the Compound of Formula
17, $R_1$=$CH_3$; $R_2$=$CH_2CH_3$)

Thionyl chloride (3.1 mL) was added slowly to a solution of the compound of formula 17 ($R_1$=$CH_3$; $R_2$=$CH_2CH_3$, 10 g) in isopropyl acetate (50 mL), acetonitrile (6.4 mL), and triethylamine (12.5 mL) at 0-5° C. After stirring for 60 minutes at this temperature, the reaction was quenched with water (40 mL). The organic layer was separated and washed with water (40 mL) followed by saturated sodium bicarbonate solution (50 mL). Acetonitrile (5 mL) and sodium bicarbonate (3.9 g) were added to the obtained organic layer and the mixture was cooled to 10-15° C. Sodium hypochlorite solution (14% available chlorine, 32.98 g) was added at 10-15° C. and the mixture was stirred vigorously at the same temperature for 30 minutes. Thereafter, the temperature was raised to 25-35° C. and the mixture was stirred for 8 hours. After completion of the reaction, the reaction mass was quenched with 15% w/w aqueous sodium sulfite solution (40 mL). The resultant mass was filtered. From the filtrate, the organic layer was separated and washed with saturated sodium bicarbonate solution. Triethylamine was added to the organic layer and the resulting solution was concentrated under reduced pressure at 40-45° C. The resulting residue was stirred in isopropyl alcohol (30 mL) at 0-5° C. The precipitated product was filtered, washed with isopropyl alcohol, and then dried at 30-35° C. under reduced pressure to yield the titled compound as a white solid (7 g).

$^1$H NMR (300 MHz, DMSO-d6): δ 1.18 (s, 3H), 1.19 (s, 3H), 1.26 (t, J=7.2 Hz, 3H), 1.83 (s, 3H), 3.16 (s, 3H), 3.22 (s, 3H), 3.54 (dd, J=3.6 Hz, 11.4 Hz, 1H), 3.67 (t, J=11.1 Hz, 1H), 4.18-4.4 (m, 3H), 5.24 (d, J=7.2 Hz, 1H).

Example 6

Preparation of the Compound of Formula 14
($R_1$=$CH_3$; $R_2$=$CH_2CH_3$)

Triethylamine (5.69 mL) and triethylamine trihydrofluoride (2.82 g) were added sequentially to the compound of formula 15 ($R_1$=$R_2$=$CH_3$, 16 g) at room temperature and the temperature was raised to 85-90° C. Stirring was continued for 5-6 hours at 85-90° C. After completion of the reaction, the reaction mass was cooled to 25-35° C. and extracted with ethyl acetate. Thereafter, the mixture was washed with 10% aqueous potassium carbonate solution followed by water. The organic layer was dried over sodium sulfate and concentrated to obtain the titled compound as a residue (15 g).

$^1$H NMR (300 MHz, DMSO-d6): δ 1.05 (s, 3H), 1.12 (s, 3H), 1.23 (t, J=7.2 Hz, 3H), 1.49 (d, J=22.8 Hz, 3H), 3.12 (s, 3H), 3.15 (s, 3H), 3.42-3.55 (m, 1H), 3.6 (dd, J=3.3 Hz, 12 Hz, 1H), 3.8 (dt, J=2.4 Hz, 10.2 Hz, 1H), 4.02-4.19 (m, 2H), 4.39 (dd, J=9.36 Hz, 25.8 Hz, 1H).

Example 7

Preparation of the Compound of Formula 13
($R_1$=$CH_3$; $R_2$=$CH_2CH_3$)

The compound of formula 14 ($R_1$=$R_2$=$CH_3$, 15 g) was diluted with tetrahydrofuran (150 mL) then stirred with sulfuric acid (0.36 g) and water (0.66 g) at −15 to −10° C. for 1 hour. The mixture was then extracted with ethyl acetate and washed with saturated aqueous sodium hydrogen carbonate solution. The obtained organic layer was washed with water, dried over sodium sulfate, and concentrated to dryness. The obtained residue was purified by column chromatography to provide the titled compound (5.5 g).

$^1$H NMR (300 MHz, DMSO-d6): δ 1.06 (s, 3H), 1.13 (s, 3H), 1.22 (t, J=7.2 Hz, 3H), 1.44 (d, J=21.9 Hz, 3H), 3.13 (s, 3H), 3.15 (s, 3H), 3.36-3.5 (m, 1H), 3.5-3.71 (m, 2H), 3.71-3.9 (m, 1H), 4.09 (q, J=7.2 Hz, 2H), 5.64 (d, J=8.4 Hz, 1H).

Example 8

Preparation of the Compound of Formula 12
($R_1$=$CH_3$; $R_2$=ethyl; $R_3$=Cinnamoyl)

4-Dimethylaminopyridine (94 mg), cinnamoyl chloride (3.86 g), and triethylamine (4.3 mL) were sequentially added to a solution of the compound of formula 13 ($R_1$=$R_2$=$CH_3$, 5 g) in acetonitrile (50 mL) at room temperature. After stirring for 16 hours at room temperature, the reaction mass was diluted with ethyl acetate (50 mL) and washed with saturated aqueous sodium hydrogen carbonate. The obtained organic layer was washed with water, dried over sodium sulfate, and concentrated to dryness. Finally, the obtained residue was purified by column chromatography to give the titled compound (1.9 g).

$^1$H NMR (300 MHz, DMSO-d6): δ 1.12 (s, 3H), 1.14 (s, 3H), 1.27 (t, J=6.9 Hz, 3H), 1.41 (d, J=21.6 Hz, 3H), 3.13 (s, 3H), 3.2 (s, 3H), 3.35-3.53 (m, 2H), 4.08 (m, 1H), 4.20 (q, J=6.3 Hz, 2H), 5.33 (dd, J=9.6 Hz, 25.8 Hz, 1H), 6.76 (d, J=15.9 Hz, 1H), 7.35-7.59 (m, 3H), 7.7-7.9 (m, 3H).

Example 9

Preparation of the Compound of Formula 10
($R_3$=cinnamoyl)

Acetic acid (7 mL) and water (3 mL) were added to the compound of formula 12 ($R_1$=$CH_3$; $R_2$=ethyl; $R_3$=cinnamoyl, 1 g) at room temperature. The reaction mixture was heated to 100-110° C. and stirred for 3-4 hours. After completion of the reaction, the reaction mass was removed under reduced pressure, diluted with methylene dichloride (20 mL and washed with saturated aqueous sodium hydrogen carbonate. The organic layer was washed with water, dried over sodium sulfate, and concentrated. Finally, the obtained residue was purified by column chromatography to get the titled compound (0.5 g).

$^1$H NMR (300 MHz, DMSO-d6): δ 1.68 (d, J=24.6 Hz, 3H), 3.62-3.82 (m, 2H), 4.65-4.8 (m, 1H), 5.35-5.5 (m, 2H), 6.75 (d, J=15.9 Hz, 1H), 7.36-7.52 (m, 3H), 7.7-7.87 (m, 3H).

Example 10

Preparation of the Compound of Formula 9
($R_3$=$R_4$=cinnamoyl)

4-Dimethylaminopyridine (0.45 g), cinnamoyl chloride (14.9 g), triethylamine (9.0 g) were added sequentially to a solution of the compound of formula 10 ($R_3$=cinnamoyl, 22 g) in acetonitrile at room temperature. Thereafter, the reaction mixture was stirred at room temperature for 16 hours, diluted with ethyl acetate (50 mL), and washed with saturated aqueous sodium hydrogen carbonate. The organic layer was washed with water, dried over sodium sulfate, and concentrated to dryness. The product was crystallized with isopropyl alcohol.

$^1$H NMR (300 MHz, DMSO-d6): δ 1.67 (d, J=24.3 Hz, 3H), 4.41-4.68 (m, 2H), 4.87-5.05 (m, 1H), 5.5-5.73 (m, 1H), 6.6-6.88 (m, 2H), 7.33-7.5 (m, 6H), 7.65-7.85 (m, 6H).

Example 11

Preparation of the Compound of Formula 8
($R_3=R_4$=cinnamoyl)

Under nitrogen atmosphere, 2,2,2-trifluoroethanol (2.89 g) was added to a solution of Vitride (10.9 g) in toluene (20 mL) at −20 to −15° C. The solution was allowed to warm to room temperature and was stirred for 60 minutes. Thereafter, the solution was added to the compound of formula 9 ($R_3=R_4$=cinnamoyl, 10 g) in methylene dichloride (50 mL) at −20 to −15° C. After stirring the reaction mass for 2 hours, the reaction was quenched at 0-5° C. in concentrated hydrochloric acid (40 mL). Water (50 mL) was then added. The resulting mixture was extracted with methylene dichloride (20 mL) and washed with 15% w/w citric acid solution (50 mL) followed by water (50 mL). The resulting organic phase was concentrated under reduced pressure to yield the compound of formula 8 ($R_3=R_4$=cinnamoyl) as an oily liquid. The liquid was then used in the next conversion (example 12) after dilution.

Example 12

Preparation of the Compound of Formula 7
($R_3=R_4$=cinnamoyl)

Under nitrogen atmosphere, N,N-dimethylformamide (1.84 g) was added to a solution of oxalyl chloride (3.17 g) in methylene dichloride (50 mL) at 0-5° C. Thereafter, the mixture was stirred for 60 minutes while maintaining the temperature below 15° C. The compound of formula 8 ($R_3=R_4$=cinnamoyl), after diluting with methylene dichloride (20 mL), was added to above reaction mass slowly while maintaining the temperature below 15° C. The resulting reaction mixture was stirred for 10-12 hours at 20-30° C. After completion of the reaction, the reaction was slowly quenched with aqueous saturated sodium bicarbonate solution (50 mL) and stirred for 15 minutes. The separated organic layer was washed with water (50 mL) and concentrated under reduced pressure to yield the compound of formula 7 ($R_3=R_4$=cinnamoyl) as an oily liquid, which can be used in the next reaction (example 13).

Example 13

Preparation of the Compound of Formula 5
($R_3=R_4$=cinnamoyl)

A solution containing N-benzoylcytosine (6 g), hexamethyldisilazane (4.49 g), and ammonium sulfate (0.06 g) in chlorobenzene (50 mL) was refluxed at 120-125° C. for 6 hours and concentrated to ~25 mL at 65-70° C. under reduced pressure. To the resulting concentrated mass, the compound of formula 7 (prepared from example 12, $R_3=R_4$=cinnamoyl) diluted in chlorobenzene (10 mL) and tin (IV) chloride (12.2 g) were added sequentially to the resulting concentrated mass at 65-70° C. and stirring was continued maintaining this temperature for 16-18 hours. After completion of the reaction, the reaction mixture was concentrated under reduced pressure to ~80 mL, cooled to 20-30° C., then slowly quenched with 30% aqueous sulfuric acid solution. The product was extracted with methylene dichloride (100 mL) and the organic layer was washed sequentially with 30% sulfuric acid, 50% acetic acid, and 6 N hydrochloric acid solution. Triethylamine (10 g) was added to the obtained organic layer, which was then concentrated under reduced pressure. Finally, the product was crystallized with methanol (100 mL) and dried under vacuum to get the compound of formula 5 ($R_3=R_4$=cinnamoyl) as an almost white solid.

Example 14

Preparation of the Compound of Formula 4

Aqueous sodium hydroxide solution in methanol ((3 mole eq. based on input) in 15 mL water, 15 mL methanol) was added to a mixture of the compound of formula 5 ($R_3=R_4$=cinnamoyl, 10 g), methanol (5 mL) and N-methylmorpholine (5 mL) at −25° C. over a period of one hour. After the reaction completed, the reaction was quenched with ~17% w/w dilute hydrochloric acid (13.2 mL) at −30 to −20° C. Thereafter, the temperature was raised to 20-25° C. and water (25 mL) was added. The solution was filtered to isolate the precipitated product which was then dried at 65-70° C. under reduced pressure to yield the compound of formula 4 as a white solid (5 g).

Example 15

Preparation of the Compound of Formula 9
($R_3$=cinnamoyl, $R_4$=benzoyloxymethyl)

4-Dimethylaminopyridine (0.45 g), benzoyl chloride (10.51 g), and triethylamine (9.0 g) were added sequentially to a solution of the compound of formula 10 ($R_3$=cinnamoyl, 22 g) in acetonitrile (25 mL) at room temperature. Thereafter, the reaction mixture was stirred at room temperature for 16 hours, diluted with ethyl acetate (50 mL), and washed with saturated aqueous sodium hydrogen carbonate. The organic layer was washed with water, dried over sodium sulfate, and concentrated to dryness. The product was crystallized with isopropyl alcohol.

$^1$H NMR (CDCl3): δ 1.73 (d, J=23.4 Hz, 3H), 4.55-4.59 (dd, J=5.1, 12.6 Hz, 1H), 4.71-4.76 (dd, J=3.5, 12.8 Hz, 1H), 4.90-4.95 (m, 1H), 5.35-5.48 (dd, J=7.4, 17.9 Hz, 1H), 6.50 (d, J=16.2 Hz, 1H), 7.39-7.60 (m, 5H), 7.52-7.59 (m, 3H), 7.8 (d, J=15.9 Hz, 1H), 8.0-8.03 (m, 2H).

Example 16

Preparation of the Compound of Formula 8
($R_3$=cinnamoyl, $R_4$=benzoyl)

Under nitrogen atmosphere, 2,2,2-trifluoroethanol (3.01 g) was added to a solution of Vitride (10.87 g) in toluene (20 mL) at −20 to −15° C. The solution was allowed to warm to room temperature and was stirred for 60 minutes. Thereafter, the solution was added to the compound of formula 9 ($R_3$=cinnamoyl, $R_4$=benzoyloxymethyl, 10 g) in methylene dichloride (50 mL) at −20 to −15° C. After stirring the reaction mass for 2 hours, the reaction was quenched at 0-5° C. with concentrated hydrochloric acid (40 mL) after which water was added. The resulting mixture was extracted with methylene dichloride (20 mL) and washed with 15% w/w citric acid solution (50 mL) followed by water (50 mL). The resulting organic layer was concentrated under reduced pressure to yield the title compound as an oily liquid, which may be used in the next conversion (example 17), after being diluted.

Example 17

Preparation of the Compound of Formula 7
($R_3$=cinnamoyl, $R_4$=benzoyloxymethyl)

Under nitrogen atmosphere, N,N-dimethylformamide (2.01 g) was added to a solution of oxalyl chloride (3.5 g) in methylene dichloride (50 mL) at 0-5° C. Thereafter, the mixture was stirred for 60 minutes maintaining the temperature below 15° C. The compound of formula 8 ($R_3$=cinnamoyl, $R_4$=benzoyl, 10 g, after diluting with methylene dichloride (20 mL), was slowly added to above reaction mass maintaining the temperature below 15° C. The resulting reaction mixture was stirred for 10-12 hours at 20-30° C. After completion of the reaction, the reaction was slowly quenched with aqueous saturated sodium bicarbonate solution (50 mL) and stirred for 15 minutes. The separated organic layer was washed with water (50 mL) and concentrated under reduced pressure to yield the title compound as an oily liquid, which can be used in the next reaction (example 18).

Example 18

Preparation of the Compound of Formula 5
($R_3$=cinnamoyl, $R_4$=benzoyl)

A solution containing $N^4$-benzoylcytosine (6.42 g), hexamethyldisilazane (4.78 g), and ammonium sulfate (0.06 g) in chlorobenzene (50 mL) was refluxed at 120-125° C. for 6 hours and concentrated to ~25 mL at 65-70° C. under reduced pressure. The compound of formula 7 (prepared from example 17, $R_3$=cinnamoyl, $R_4$=benzoyl) diluted in chlorobenzene (10 mL) and tin (IV) chloride (13.01 g) were added sequentially to the resulting concentrated mass at 65-70° C. Stirring was continued at this temperature for 16-18 hours. After completion of the reaction, the reaction mixture was concentrated under reduced pressure to ~80 mL, cooled to 20-30° C., and slowly quenched with 30% aqueous sulfuric acid solution. The product was extracted with methylene dichloride (100 mL) and the organic layer was washed sequentially with 30% sulfuric acid, 50% acetic acid, and 6N hydrochloric acid solution. Triethylamine (10 g) was added to the obtained organic layer which was then concentrated under reduced pressure. Finally, the product was crystallized with methanol (100 mL) and dried under vacuum to get the title compound as an almost white solid.

$^1$H NMR (DMSO-d6): δ 1.40 (d, J=23.1 Hz, 3H), 4.58-4.70 (m, 3H), 5.68 (d, J=6.6 Hz, 1H), 6.22-6.28 (m, 1H), 6.75 (d, J=16.2 Hz, 1H), 7.36-7.79 (m, 13H), 8.00-8.01 (m, 4H), 8.27 (d, J=7.5 Hz, 1H), 11.41 (s, 1H).

Example 19

Preparation the Compound of Formula 4

Aqueous sodium hydroxide solution in methanol (3 mole eq. based on input) in 15 mL water, 15 mL methanol,)) was added to a mixture of the compound of formula 5 ($R_3$=cinnamoyl, $R_4$=benzoyloxymethyl, 10 g), methanol (5 mL), and N-methylmorpholine (5 mL) at −25° C. over a period of one hour. After the reaction completed, the reaction mass was quenched with ~17% w/w dilute hydrochloric acid (13.2 mL) at −30 to −20° C. Thereafter, the temperature was raised to 20-25° C. and water (25 mL) was added. The solution was filtered to obtain the precipitated product which was then dried at 65-70° C. under reduced pressure to yield the compound of formula 4 as a white solid (5 g).

$^1$H NMR (DMSO-d6): δ 1.25 (d, J=22.5 Hz, 3H), 3.66-3.70 (m, 1H), 3.87-3.92 (m, 3H), 5.39 (s, 1H), 5.72 (d, J=6.3 Hz, 1H), 6.17 (d, J=18.3 Hz, 1H), 7.4 (d, J=7.2 Hz, 1H), 7.50-7.55 (m, 2H), 7.61-7.66 (m, 1H), 8.01 (d, J=7.2 Hz, 2H), 8.52 (d, J=7.5 Hz, 1H), 11.36 (s, 1H).

Example 20

Preparation of the Compound of Formula 2
(N-benzoyl sofosbuvir)

Under dry and inert atmosphere, diisopropylethylamine was added over a period of 60 minutes at 25-35° C. to a mixture of the compound of formula 4 (5 g), (S)-2-[(S)-(2,3,4,5,6-pentafluoro-phenoxy)-phenoxy-phosphorylamino]propionic acid isopropyl ester (formula 3, 7.45 g) and anhydrous magnesium chloride (1.57 g) in tetrahydrofuran (50 mL). Stirring was continued at 25-35° C. for 16 hours to complete the reaction which was then quenched with ~10% w/w aqueous ammonium chloride solution (35 mL). Isopropyl acetate (50 mL) was added and the layers were separated. The organic layer was washed sequentially with ~10% w/v hydrochloride solution (35 mL), 5% w/v aqueous sodium bicarbonate solution (35 mL), 10% w/v hydrochloride solution (35 mL), and 10% w/v aqueous sodium chloride solution. Thereafter, the organic layer was concentrated under reduced pressure at 45-50° C. to yield a white solid which was crystallized/purified with isopropyl acetate and dried at 50-55° C. under reduced pressure to yield the compound of formula 2 (N-benzoyl sofosbuvir, 6 g).

$^1$H NMR (DMSO-d6): δ 1.14-1.28 (m, 12H), 3.82-3.84 (m, 2H), 4.07 (s, 1H), 4.31-4.40 (m, 2H), 4.82-4.86 (m, 2H), 5.89 (s, 1H), 6.10-6.23 (m, 2H), 7.16-7.66 (m, 9H), 7.99-8.07 (m, 3H), 11.37 (s, 1H).

Example 21

Preparation of the Compound of Formula 2
(N-benzoyl sofosbuvir)

Tert-butyl magnesium chloride (14.5 mL) was added over a period of ~30 minutes at 20-25° C. under dry nitrogen atmosphere to a mixture of the compound of formula 4 (5 g) and (S)-2-[(S)-(2,3,4,5,6-pentafluoro-phenoxy)-phenoxy-phosphorylamino]propionic acid isopropyl ester (formula 3, 7.45 g) in tetrahydrofuran (100 mL). After completion of the reaction, saturated ammonium chloride (50 mL) was added slowly at 20-25° C. to quench the reaction mass. Ethyl acetate (50 mL) was added, the mixture was stirred, and the layers were separated. The organic layer was washed sequentially with 5% w/v aqueous sodium bicarbonate (25 mL) and water (25 mL) at 20-25° C. The obtained organic layer was concentrated under reduced pressure at 45-50° C. Ethyl acetate (30 mL) was added to the residue and the mixture was heated to 60-65° C. After stirring for ~30 minutes at 60-65° C., the obtained slurry product was slowly cooled to 0-5° C. over a period of ~90 minutes. After stirring for ~2 hours at 0-5° C., the solution was filtered to obtain a product which was washed with pre-cooled ethyl acetate (10 mL, 5° C. and dried at 50-55° C. to yield formula 2 (N-benzoyl sofosbuvir, 6.75 g).

Example 22

Preparation of Sofosbuvir

N-benzoyl sofosbuvir (6 g) was added to a mixture of 1,2-dimethoxyethane (69 mL), water (60 mL), and citric acid (1.08 g) and the contents were stirred at 75-85° C. for 40-50 hours. After completion of the reaction, the reaction mass was concentrated under reduced pressure and the obtained residue was dissolved in isopropyl acetate (60 mL). The solution was washed with ~10% w/w aqueous hydrochloric acid (3×60 mL) and ~10% w/v aqueous sodium chloride solution. The organic layer was concentrated under reduced pressure at 50-55° C. and the resulting concentrated mass was dissolved in methylene dichloride (36 mL). Diisopropyl ether (126 mL) was added to precipitate the product. After stirring at 20-25° C. for 16 hours, the solution was filtered to result in a solid which was washed with a methylene dichloride/diisopropyl ether mixture and dried under reduced pressure to yield sofosbuvir (3.6 g).

Example 23

Preparation of Sofosbuvir

N-Benzoyl Sofosbuvir (6 g) was added to a mixture of 1, 2-dimethoxyethane (69 mL), water (60 mL) and citric acid monohydrate (1.2 g) and the contents were stirred at 75-84° C. for 40-50 hours. After completion of the reaction, the reaction mass was concentrated under reduced pressure and the obtained residue was dissolved in 1, 2-dimethoxyethane (16.2 mL) and water (10.8 mL). The solution was filtered through Hyflo and the obtained filtrate was added to another flask containing water (114 mL) to precipitate a solid. After stirring at 20-25° C. for 16 hours, the solution was filtered, and the obtained product was washed with water, then dried under reduced pressure to yield of Sofosbuvir (3.0 g).

Example 24

Preparation of Amorphous Sofosbuvir

Sofosbuvir (3 g) was dissolved in methanol (24 mL). The solution was filtered and the obtained filtrate was concentrated under reduced pressure at <45° C. to get a frothing solid/solid which was stirred with n-heptane (21 mL) to precipitate amorphous sofosbuvir (54.0%).

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

We claim:
1. A process for the preparation of compound of formula 9

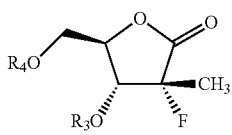

comprising the steps of
a) converting a compound of formula 17 to a compound of formula 16;

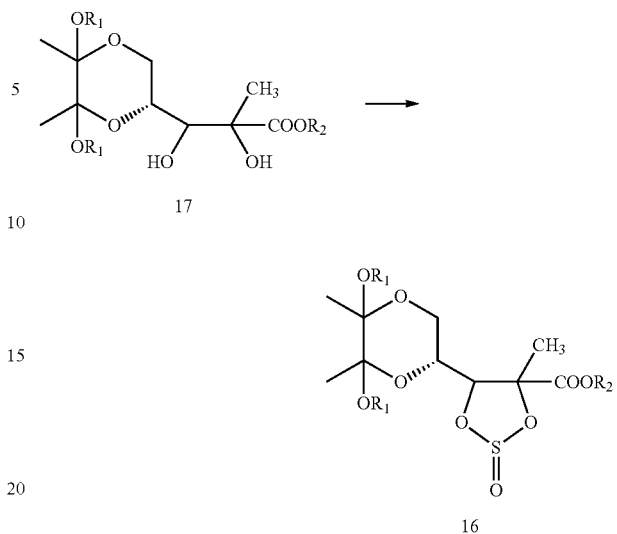

b) oxidizing the compound of formula 16 to get a compound of formula 15;

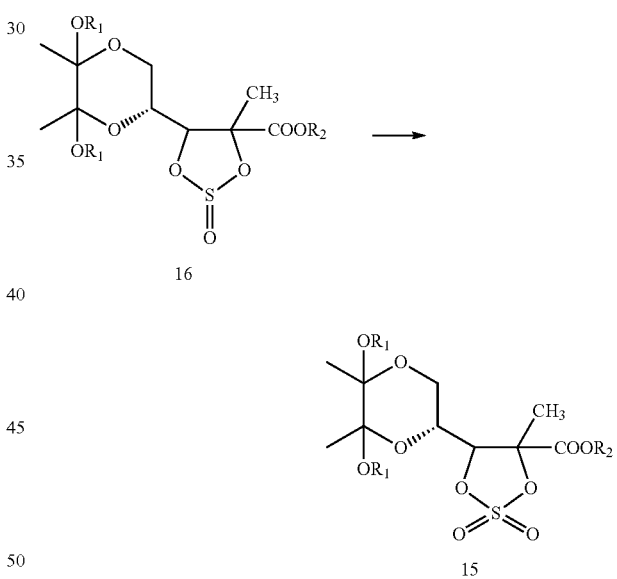

c) fluorinating the compound of formula 15 to obtain fluoro sulfate compound of formula 14;

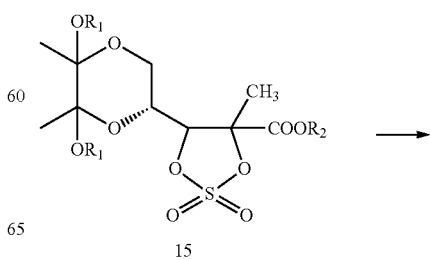

-continued

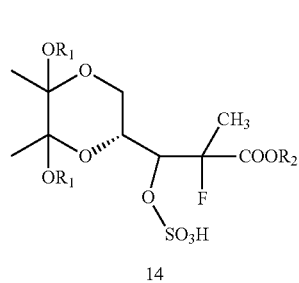
14 d) hydrolyzing the compound of formula 14 to yield a compound of formula 13;

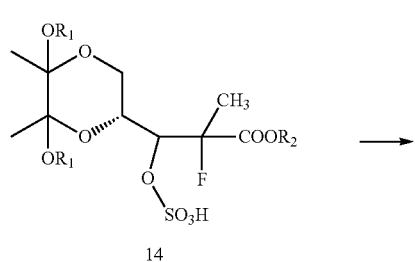
14

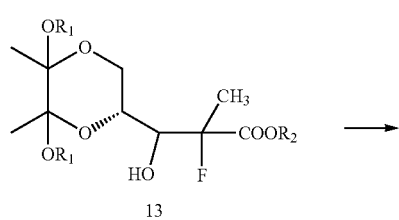
13 e) protecting the hydroxyl group of the compound of formula 13 to get a compound of formula 12, and

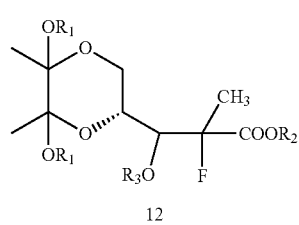
12 f) converting the compound of formula 12 to a compound of formula 9

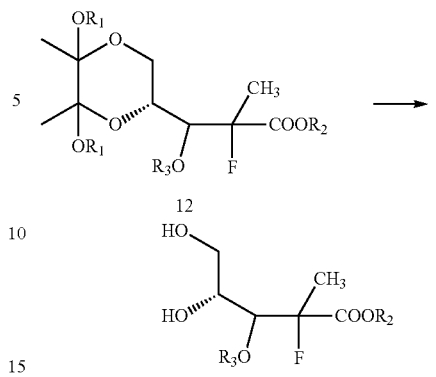

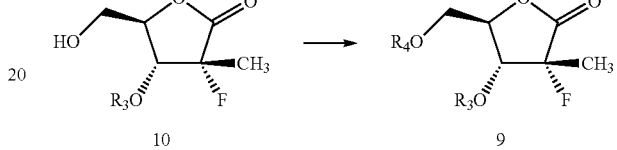

wherein $R_1$ and $R_2$ are independently selected from the group consisting of hydrogen, $C_1$-$C_{10}$ alkyl, aryl, $C_1$-$C_{10}$ aralkyl; $R_3$ is cinnamoyl or heteroaryl; and $R_4$ is selected from the group consisting of hydrogen, alkyl, aryl, aralkyl, benzoyl, cinnamoyl, and heteroaryl.

2. The process according to claim 1, wherein the step of converting the compound of formula 17 to the compound of formula 16 is performed in the presence of a thionyl chloride and a base.

3. The process according to claim 2, wherein the base is selected from the group consisting of alkali metal hydroxides, alkali metal carbonates, amine bases, alcoholic amine bases, and mixtures thereof.

4. The process according to claim 1, wherein the oxidizing agent is selected from the group consisting of sodium hypochlorite, peroxides, and mixtures thereof.

5. The process according to claim 1, wherein the compound of formula 17 may be directly converted to the compound of formula 15 by reacting the compound of formula 17 with a sulfonating agent in the presence of a base.

6. The process according to claim 5, wherein the sulfonating agent selected from the group consisting of sulfuryl chloride, sulfuryl fluoride, and mixtures thereof.

7. The process according to claim 5 wherein the base is selected from the group consisting of alkali metal hydroxides, alkali metal carbonates, amine bases, alcoholic amine bases and mixtures thereof.

8. The process according to claim 1, wherein the step of fluorinating the compound of formula 15 to the compound of formula 14 is performed in the presence of a fluorinating agent.

9. The process according to claim 7, wherein the fluorinating agent is selected from the group consisting of hydrogen fluoride, tetraethylammonium fluoride, tetrabutylammonium fluoride, and mixtures thereof.

10. The process according to claim 1, wherein the hydrolyzing of formula 14 is carried out in the presence of an acid.

11. The process according to claim 9, wherein the acid is selected from the group consisting of hydrochloric acid, hydrobromic acid, sulfuric acid, formic acid, acetic acid, fumaric acid, oxalic acid, and mixtures thereof.

12. The process according to claim 1, wherein the step of converting the compound of formula 12 to the compound of formula 9 is performed in the presence of an acid.

13. The process according to claim 11, wherein acid is selected from the group consisting of hydrochloric acid, hydrobromic acid, sulfuric acid, formic acid, acetic acid, trifluoro acetic acid, fumaric acid, oxalic acid, and mixtures thereof.

14. The process according to claim 1, further comprising converting the compound of formula 9 into sofosbuvir.

15. A compound of formula 12a

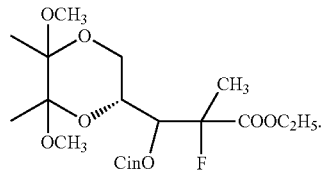

* * * * *